United States Patent
Riegel

(10) Patent No.: US 6,369,579 B1
(45) Date of Patent: Apr. 9, 2002

(54) METHOD FOR DETERMINING THE ELECTRICAL CONDUCTIVITY OF FLUIDS

(75) Inventor: Harald Riegel, Stuttgart (DE)

(73) Assignee: Endress +Hauser Conducta Gesellschaft fur Mess- und Regeltechnik mbH+Co., Gerlingen (DE)

( * ) Notice: Subject to any disclaimer, the term of this patent is extended or adjusted under 35 U.S.C. 154(b) by 0 days.

(21) Appl. No.: 09/407,870

(22) Filed: Sep. 29, 1999

(30) Foreign Application Priority Data

Sep. 29, 1998 (DE) .......................................... 198 44 489

(51) Int. Cl.⁷ ............................................... G01N 27/02
(52) U.S. Cl. ...................................... 324/439; 324/425
(58) Field of Search ................................ 324/439, 446, 324/445, 450, 425

(56) References Cited

U.S. PATENT DOCUMENTS

| | | | |
|---|---|---|---|
| 5,260,663 A | * | 11/1993 | Blades ........................ 324/442 |
| 5,489,849 A | * | 2/1996 | Sadoway et al. ............ 324/447 |
| 5,612,621 A | * | 3/1997 | Yang .......................... 324/439 |

FOREIGN PATENT DOCUMENTS

| | | |
|---|---|---|
| DE | 4233110 A1 | 4/1994 |
| EP | 0580326 A1 | 1/1994 |
| EP | 0911639 A1 | 4/1999 |

* cited by examiner

*Primary Examiner*—Peter S. Wong
*Assistant Examiner*—Lawrence Luk
(74) *Attorney, Agent, or Firm*—Jones,Tullar & Cooper, P.C.

(57) ABSTRACT

Present invention relates to a process for determining the electrical conductivity of fluids by means of conductively operable conductivity measuring cells using analysis and processing measurement technology, wherein the conductivity of the fluid is determined from a measured resistance value and the geometric measuring cell constants (k); in order to reduce error in the determination of the electrical conductivity, this is determined in the following manner:

by using a measurement converter, the impedance of the measuring cell immersed in the fluid is determined for at least two frequency values of an alternating voltage, the frequency-independent parameters (n, Q) and the desired resistance ($R_{f1}$) are determined based on the determined impedance values and based on an equivalent circuit diagram comprised of a parallel connection of a capacitor ($C_{cell}$) representing the measuring cell capacitance, an ohmic resistance ($R_{f1}$) representing the desired resistance of the fluid inside the conductivity measuring cell, and a component ($Z_{M/F1}$) that has electrical, frequency-independent parameters (n, Q) and a frequency-independent phase, wherein the latter ($R_{f1}$, $Z_{M/F1}$) are connected in series with each other.

7 Claims, 1 Drawing Sheet

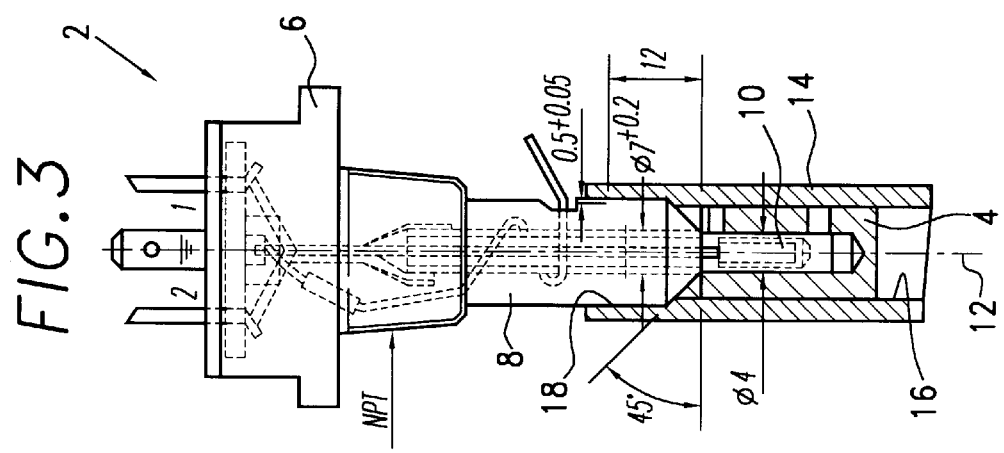
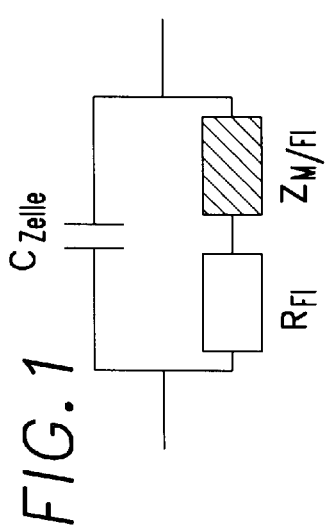
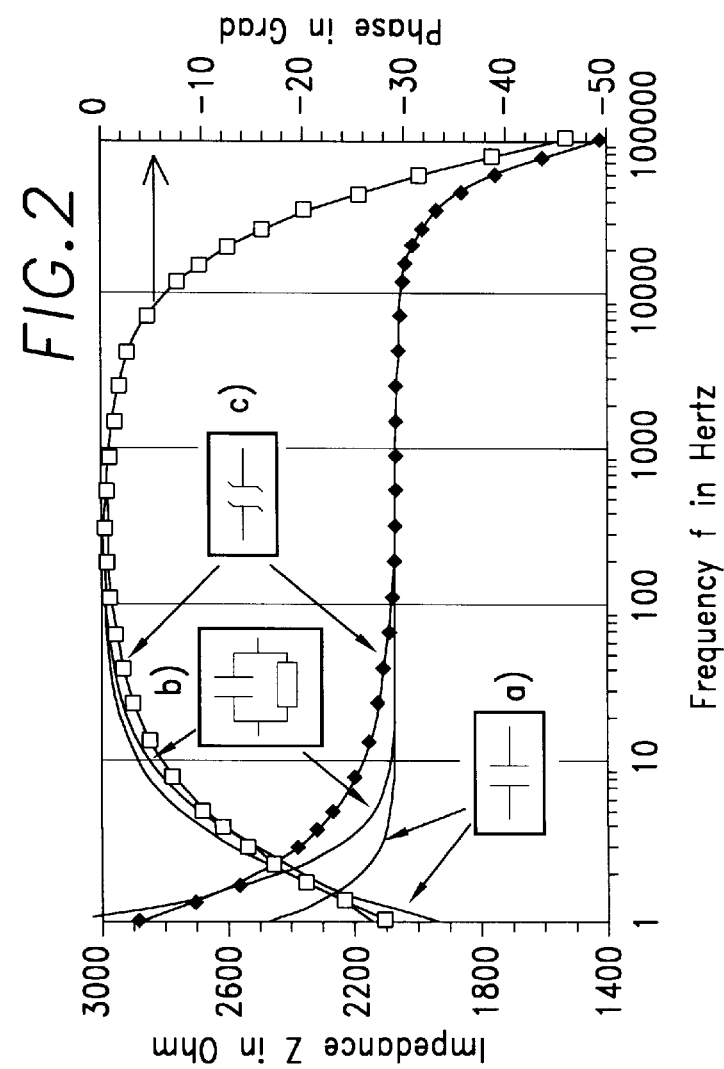

METHOD FOR DETERMINING THE ELECTRICAL CONDUCTIVITY OF FLUIDS

FIELD OF THE INVENTION

The present invention relates to a process for determining the electrical conductivity of fluids by means of conductively operable conductivity measuring cells using analysis and processing measurement technology, wherein the conductivity of the fluid is determined from a measured resistance or impedance value and the geometric measuring cell constants.

BACKGROUND OF THE INVENTION

A conductively operable conductivity measuring cell is understood to mean one in which electrodes are disposed in immediate contact with the fluid to be measured. In order to determine the electrolytic conductivity of the fluid, the resistance or conductance of the electrode measurement path in the fluid is determined, for example, by using an alternating current measuring bridge. If the cell constant k is known, then the electrolytic conductivity ó can be determined.

In contrast to the conductive conductivity measurement, there is also the principle of inductive conductivity measurement through the use of an electrodeless conductivity measuring cell in which the fluid to be measured is used as an inductively acting coupling medium between an excitation coil and a measurement coil. The present invention, however, relates to the conductive conductivity measurement.

The physical interrelationships of current conduction in electrolyte fluids are as follows:

Depending on the dissociation behavior, the electrolytic components under consideration in the fluid are broken down to a greater or lesser extent into their ions (dissociated). These ions are responsible for the electrical current transport in the fluid. The actual degree of dissociation of an electrolyte therefore depends on the temperature and on the concentration of this material in the fluid. The carrier medium as such, for example the water in aqueous solutions, also contributes to the conductivity by means of dissociation. Over wide regions, the electrolytic conductivity increases along with the concentration of the electrolytes.

In addition to the determination of the pH value, the measurement of the electrolytic conductivity also represents a simple, high-precision means for analysis and process control, particularly with automated processes.

The electrolytic conductivity ó of a fluid is defined as the product of a geometric constant of the electrode measuring cell, the so-called cell constant k, and the reciprocal electrical, ohmic resistance of the fluid between the electrodes.

$$\sigma = k \cdot \frac{1}{R}$$

For a measurement path with a length L and a cross sectional area A with a corresponding area A of the electrodes, the electrical resistance R that can be determined as a measurement quantity is produced as the product of the specific resistance ñ and the quotient length/area, i.e. L/A $$R = \rho \cdot \frac{L}{A}$$

Therefore the specific resistance ñ can be calculated from the electrical resistance measured since its reciprocal value is defined as the conductivity ó. Consequently the following is true:

$$\rho = R \cdot \frac{A}{L}$$

$$\sigma = \frac{1}{\rho} = \frac{1}{R} \cdot \frac{L}{A}$$

The geometric constant mentioned at the beginning (cell constant) of this particular electrode measurement path is therefore L/A.

The measurement range of a conductivity measuring cell is limited on the one hand to a high conductivity by the physical events of the phase transition from the solid metal electrode into the fluid. In the ideal case, this impedance of the phase transition behaves in a purely capacitive manner, in fact because of the electrochemical double layer being formed. Actually, however, the impedance of this phase transition also has a real, i.e. ohmic component. The measurement result is therefore distorted if this real part of the impedance of the phase transition is non-negligible in relation to the resistance of the fluid that is of interest. This limits the measurement range of a conductivity measuring cell toward the top since up till now, only the ohmic resistance of the fluid and not that of the phase transition from the solid metal electrode into the fluid was taken into consideration in the evaluation.

SUMMARY OF THE INVENTION

Based on this, the object of the current invention is to reduce errors in the determination of conductivity according to the process of the type mentioned at the beginning.

This object is attained by means of a process of the type mentioned at the beginning, which according to the present invention is characterized by means of the following process steps:

By using a measurement converter, the impedance of the measurement cell immersed in the fluid is determined in at least two frequency values of an alternating current; the frequency-independent parameters n, Q and the desired resistance R are determined from the determined impedance values, on the basis of an equivalent circuit diagram comprised of a parallel connection of a capacitor C representing the measuring cell capacitance, an ohmic resistance $R_{f1}$ representing the desired resistance of the fluid inside the conductivity measurement cell, and component Z that has an electric, frequency-independent parameter n, Q with a frequency-independent phase, wherein the latter R, Z are connected to each other in series.

After the desired resistance $R_{f1}$ has been determined in the above manner, the conductivity ó can be calculated based on the interrelationship described at the beginning between the resistance $R_{f1}$ and the conductivity ó through the use of cell constants k ($\sigma=1/R_{f1}\cdot k$).

Since the physical events at the phase transition from the solid metal electrode to the fluid can be taken into account according to the present invention, by virtue of the fact that according to the present invention, the ohmic resistance $R_{f1}$, which alone can be attributed to the measurement fluid that is of interest, is determined by means of calculation from a number of measurement values on the basis of the above-described equivalent circuit diagram, errors in the determination of the electrolytic conductivity in the region of the upper end of the given measurement range for a specific measurement cell device can be reduced. In other words, the conductivity measurement range of a particular measuring cell device can be extended upward. This can achieve a measurement range extension by a factor of 10.

According to a preferred embodiment of the present invention, the component which is intended to simulate the physical events in the region of the phase transition from the solid metal electrode to the fluid comprises two frequency-independent parameters and, in order to be able to calculate these parameters as well as the desired resistance, a measurement of the real part and the imaginary part of the impedance of the measurement cell immersed in the fluid is respectively determined at two frequency values.

However, if only measurement converters are available to carry out the process, in which the real part or the amount of the impedance of the measuring cell device immersed in the fluid can be determined, then impedance measurements in at least three frequency values are required.

It should also be noted at this point that the present invention turns out to be particularly advantageous for the measurement of the electrical conductivity of fluids in the measurement range of less than 200 $\mu$S/cm, in particular of less then 100 $\mu$S/cm, because by means of the measurement range extension according to the invention, calibrating solutions can use whose conductivity values previously could not lie within the measurement range of respectively considered conductivity measuring cell. To this extent, it turns out to be particularly advantageous that the conductivity measurement range, for example of a super-clean water measuring cell with a cell constant of 0.01 cm$^{-1}$ can be increased from approximately 20 $\mu$S/cm to 200 $\mu$S/cm. However, this offers the possibility of calibrated this conductivity measuring cell by using a calibrating solutions in the conductivity range from 100 to 200 $\mu$S/cm, for example by means of using calibrating solutions according to DIN EC 746-3, ASTM 1125-91.

The calibration of conductivity measuring cell is understood to mean the determination of the geometric cell constant k, which was calculated at the beginning as L/A with a cylindrical electrode measuring path.

Since exact calibrating solutions that are reproducible and independent of other variables are no longer available in the conductivity range below 100 $\mu$S/cm, previously, in order to determine the geometric cell constant k of a conductivity measuring cell, an additional conductivity measuring cell had to be used, whose measurement range, which satisfied the precision requirements on the one hand, overlapped at the upper end, i.e. the end coming from higher conductivities, with the measurement range in question belonging to the sensor to be calibrated and on the other hand, extended upward until sufficiently reproducible calibrating solutions could be used. In such an instance, therefore, a first conductivity measuring cell was first calibrated in the upper conductivity measurement range and using this cell, then the conductivity measuring cell in question was calibrated in the very low conductivity range. Due to the upward measurement range extension according to the invention, this is no longer necessary because there are calibrating solutions with a conductivity of 149.6 $\mu$S/cm, for example, in the range between 100 and 200 $\mu$S/cm, for example.

The calibration, i.e. the determination of the geometric cell constants of conductivity measuring cells is generally required since due to assembly-induced imprecisions, the cell constants, if they were to be determined only by means of calculation, would not correspond to the required precision of e.g. 0.5%. Since the cell constant of a conductivity measuring cell with cylindrical electrodes is determined by means of the equation:

$$k = \frac{1}{1} \cdot \ln\frac{R}{r}$$

l=length of the device
R=internal radius of the outer electrode
r=external radius of the inner electrode In the manufacture of the measuring cell the concentric disposition of the inner electrode turns out to be problematic. The error attributed to this is therefore given by means of the equation:

$$\frac{\Delta k}{k} \frac{\Delta r}{r} \cdot \frac{1}{\ln\frac{R}{r}}$$

Therefore another object is to reduce these structurally induced imprecisions.

This is attained in accordance with the other concept of the present invention by means of a process for producing a conductivity measuring cell with cylindrical, concentric electrodes that are supported on a base body, which is preferably cast out of plastic and contains the electrical supply, wherein the inner electrode is permanently mounted on a retaining pin and then the outer electrode is placed over the inner electrode and thereby brought into a positively or frictionally engaging connection with a section of the base body that is greater in diameter than the inner electrode, wherein the process is characterized in that before the mounting of the inner electrode, mounting means is slid onto the above-mentioned section of the base body and is used as a guide means for the outer circumference of the inner electrode when this is slid onto the retaining pin.

According to the present invention, this achieves the fact that the inner electrode is concentrically mounted exactly in relation to the geometric longitudinal central axis. It is now possible by using the mounting means so that a calibration of conductivity measuring cells produced in this manner can be eliminated. The cell constant is calculated by means of a simplified testing of the geometry.

The mounting means mentioned above is preferably sleeve-shaped, but this does not necessarily have to be the case since the mounting means is withdrawn again after the inner electrode is slid on. The mounting means has a guide section that is cylindrical on the inside, whose internal diameter corresponds to the external diameter of the inner electrode so that when slid onto the retaining pin, this inner electrode undergoes centering and guidance.

With a section that is larger in diameter than the guide section, the mounting means itself is advantageously fixed temporarily, i.e. during the mounting of the inner electrode, to a section of the base body mentioned above. After the withdrawal of the mounting means, this section of the base body then constitutes a guide means for the outer electrode. Advantageously, the axial extension of this section is approximately 50% of the axial length of the outer electrode so that a satisfactory centering can be achieved by means of this, i.e. a concentric disposition of the outer electrode.

Reference has already been made at the beginning to the problem that calibrating solutions in the conductivity measurement range below 100 µS/cm are either unavailable or are not independent of other variables. This turns out to be problematic particularly in conductivity measuring cells for determining the conductivity in the manufacturing of super-clean water through the use of relevant known filter technology. Therefore according to another independent concept of the present invention, the proposal is made to use already defined super-clean water as a calibration fluid. The conductivity of super-clean water at 25° C. is known with a precision of 0.3%. Super-clean water with an analysis certificate from the manufacturer is available on the market, which has conductivity of 55 nS/cm at 25° C. If super-clean water is used as a calibrating solution, then a significantly more precise cell constant determination can be achieved with the conductivity measuring cells that are used in processes for producing super-clean water. The use of a measuring cell that is calibrated at higher conductivities for calibrating the measuring cell for the very low conductivity range can therefore be eliminated.

BRIEF DESCRIPTION OF THE DRAWINGS

Other details, features, and advantages of the present invention ensue from the following description of the process according to the present invention and its backgrounds and advantages in conjunction with the accompanying FIGS.

FIG. 1 depicts an equivalent circuit diagram used for carrying out the process according to the present invention;

FIG. 2 shows an impedance spectrum including the impedance and the phase of an electrode measurement path immersed in a fluid to be measured as a function of the frequency of an excitation voltage, measured and calculated for three models of the impedance $Z_{m/f1}$;

FIG. 3 is a partially sectional depiction of a conductivity measuring cell with a mounting sleeve for the inner electrode.

DESCRIPTION OF THE PREFERRED EMBODIMENT

FIG. 1 depicts an equivalent circuit diagram of an electrode measuring device of a conductivity measuring cell immersed in an electrolytic fluid. The equivalent circuit diagram is comprised of two arms connected in parallel, wherein the one arm is comprised of a capacitor $C_{cell}$ whose capacitance represents the capacitance of the electrode device and the other arm is comprised of a series connection of a resistance $R_{f1}$ and a component $Z_{M/f1}$. The resistance $R_{f1}$ represents the ohmic resistance of the applicable fluid. The component $Z_{M/f1}$ represents or simulates the events of the phase transition between the solid metal electrode and the fluid.

The impedance Z of the measuring electrode device immersed in the measurement fluid measured at a multitude of frequencies is graphically plotted in FIG. 2 with solid black measurement points. The hollow measurement points represent the simultaneously measured phase position of the current as a response to the excitation voltage.

Different arrangements of the component $Z_{M/f1}$ have then been made in the form of the solid lines, on the basis of the equivalent circuit diagram according to FIG. 1. The two curves according to the letter a) represent the calculated impedance Z as well as the phase on the basis of the component $Z_{M/f1}$ in the form of a capacitor (purely capacitive).

A better result is supplied by arrangement b), according to which the component Z has been represented in the form of a parallel connection of a resistance and a capacitor. The best results, however, were achieved with a component c). The impedance of this component is as follows:

$$Z_{M/f1} = \frac{1}{(i\omega/\omega_o \cdot Q)^n}$$

The component has two frequency-independent parameters n and Q.

On the basis of the above-mentioned component, there are therefore two frequency-independent parameters n and Q, wherein the resistance $R_{f1}$ of the fluid to be determined represents a third parameter, i.e. a third unknown. If a suitable measurement converter is used to measure both the real part ($Z^1$) and the imaginary part ($Z^{11}$) of the impedance to be determined, then two measurements at different frequencies are sufficient in order to calculate the unknowns by means of the four variables.

With a cell capacitance of $C_{cell}$=805 pF and a value $\omega_0$ of 2π·1 Hz, the values n=0.766, Q=170 µs, and a resistance of the measurement fluid of R=2063 Ohm are calculated.

The desired fluid resistance R is calculated as follows:

$$R_{FI} = \frac{Z^1(\omega_2)Z^{11}(\omega_1) - Z^1(\omega_1)Z^{11}(\omega)}{Z^{11}(\omega_1) - Z^{11}(\omega_2)}$$

If only one measurement converter is available in which the real part or the amount of the impedance can be measured, then measurements at three different frequencies are required in order to determine the three unknowns. An evaluation of the linear, independent equation yields a transcendent equation system which generally cannot be exactly solved, but requires a numerical treatment. However, there is an exact solution for the following frequency relationship f3=10f2=100f1, according to which the fluid resistance is calculated according to the equation $$R_{FI} = \frac{Z^1(\omega_1)Z^1(\omega_2) - Z^{-1}(\omega_3)^2}{Z^1(\omega_1) + Z^1(\omega_2) + 2Z^1(\omega_3)}$$

The ohmic resistance $R_{F1}$, i.e. the real part of the total impedance of the measuring electrode device immersed in the measurement fluid, which goes back to the fluid to be determined, can be calculated in accordance with the available measurement converters. Based on this ohmic resistance, through the multiplication of its reciprocal value with the geometric cell constant k of the measuring electrode device, the conductivity ó of the fluid can be determined.

The geometric cell constant k of the conductivity measuring cell is preferably determined by measuring the ohmic resistance of the measuring cell device immersed in the calibration fluid.

FIG. 3 is a partially sectional depiction of a conductivity measuring cell with cylindrical electrodes, wherein only an inner electrode 4 is depicted. The conductivity measuring cell 2 includes a base body 6 cast of epoxy resin. The base body 6 includes a first section 8 and a retaining pin 10 protruding from the end face of the section 8. The inner electrode 4 can be slid onto the retaining pin 10. A mounting sleeve 14 is slid onto the first section 8 previously so that the inner electrode 4 is mounted on the retaining pin 10, exactly concentric to the indicated longitudinal central axis 12 of the device. The mounting sleeve 14 includes a guide section 16 which has an internal diameter that corresponds exactly to the outer diameter of the inner electrode 4. It is slid with a section 18 that has a comparatively larger diameter onto the first section 8 of the base body 6. After the mounting of the inner electrode 4, the mounting sleeve 14 is withdrawn and an outer electrode, not shown, is slid onto the first section 8 of the base body 6. In this connection, the outer electrode extends essentially over the entire axial length of the first section 8 and thus is given an exact positioning concentric to the longitudinal central axis 12. The conductivity measuring cell produced in this manner does not require any experimental calibration, but the cell constant k can be determined with sufficient precision by means of a simplified testing of the cell geometry.

What is claimed is:

1. A process for determining the electrical conductivity of fluids by means of conductively operable conductivity measuring cells, comprising the steps of:

immersing a measuring cell in the fluid;

measuring the impedance of the immersed measuring cell using a measurement converter, said impedance being determined for at least two frequency values of an alternating current;

constructing an equivalent circuit having a parallel connection of a capacitor ($C_{cell}$) representing the measuring cell capacitance, an ohmic resistance ($R_{f1}$) representing the desired resistance of the fluid inside the conductivity measuring cell, and a component ($Z_{m/F1}$) that has electrical, frequency-independent parameters (n, Q) and a frequency-independent phase, wherein the ohmic resistance and the component are connected in series with each other; and determining the frequency-independent parameters (n, Q) and the desired resistance ($R_{f1}$) based upon the measured impedance values and the equivalent circuit.

2. The process as defined in claim 1, further comprising the step of:

determining the respective measurement of a real part ($Z^{11}$) and an imaginary part ($Z^1$) of the impedance of the measuring cell immersed in the fluid by two frequency values ($\omega_1$, $\omega_2$), and wherein the frequency-dependent parameters (n, Q) and the desired resistance ($R_{f1}$) are calculated based on the determination of the measurement of the real part ($Z^{11}$) and the imaginary part ($Z^1$) of the impedance of the measuring cell immersed in the fluid.

3. The process as defined in claim 1, further comprising the step of:

determining the respective measurement of only the real part of the impedance by at least three frequency values ($\mu_1$, $\mu_2$, $\mu_3$), and wherein the frequency-dependent parameters (n, Q) and the desired resistance ($R_{f1}$) are calculated based on said determining the respective measurement of only the real part of the impedance.

4. The process as defined in claim 1, wherein the component ($Z_{M/F1}$) is defined as follows:

$$Z_{M/FI} = \frac{1}{(i\omega/\omega_o) \cdot Q}.$$

5. The process as defined in claim 3, wherein the frequency values are selected as follows:

$\omega_1=10$ and $\omega_2=100\omega_1$.

6. The process as defined in claim 1, further comprising the step of:

using a calibrating solution to determine the geometric cell constant (k) of the conductivity measuring cell for determining the electrical conductivity of fluids in the measurement range of less than 200 $\mu$S/cm.

7. The process as defined in claim 6, wherein the calibrating solution has a conductivity in the range from 100 to 200 $\mu$S/cm.

* * * * *